United States Patent
Erbacher et al.

(10) Patent No.: US 9,506,107 B2
(45) Date of Patent: Nov. 29, 2016

(54) METHOD FOR EXTRACTING NUCLEIC ACID FROM BLOOD

(75) Inventors: Christoph Erbacher, Haan (DE); Ralf Himmelreich, Langenfeld (DE); Ralf Peist, Lieden (DE); Ingerlise Evans Haaland, Kjeller (NO); Hege Hardersen, Osteras (NO)

(73) Assignee: QIAGEN GMBH, Hilden (DE)

(*) Notice: Subject to any disclaimer, the term of this patent is extended or adjusted under 35 U.S.C. 154(b) by 2580 days.

(21) Appl. No.: 12/064,321

(22) PCT Filed: Jul. 25, 2006

(86) PCT No.: PCT/EP2006/064652
§ 371 (c)(1),
(2), (4) Date: Jun. 19, 2008

(87) PCT Pub. No.: WO2007/023057
PCT Pub. Date: Mar. 1, 2007

(65) Prior Publication Data
US 2009/0018323 A1    Jan. 15, 2009

(30) Foreign Application Priority Data
Aug. 24, 2005  (DE) .................. 10 2005 040 259

(51) Int. Cl.
*C12Q 1/68* (2006.01)
*C08F 8/30* (2006.01)
*C08F 8/40* (2006.01)
*C12N 5/00* (2006.01)

(52) U.S. Cl.
CPC .............. *C12Q 1/6813* (2013.01); *C08F 8/30* (2013.01); *C08F 8/40* (2013.01); *C12N 5/0081* (2013.01); *C12Q 1/6806* (2013.01); *C12Q 1/6844* (2013.01)

(58) Field of Classification Search
None
See application file for complete search history.

(56) References Cited

U.S. PATENT DOCUMENTS

| 5,508,164 A | 4/1996 | Kausch et al. |
| 6,670,128 B2 * | 12/2003 | Smith et al. .................. 435/6.16 |
| 2007/0207460 A1 * | 9/2007 | Wambutt et al. .................. 435/6 |
| 2008/0299557 A1 * | 12/2008 | Himmelreich et al. .......... 435/6 |

FOREIGN PATENT DOCUMENTS

| EP | 0389063 | 10/2006 |
| WO | WO 97/11160 | 3/1997 |
| WO | WO 9711160 A1 * | 3/1997 |
| WO | WO 99/07749 | 2/1999 |
| WO | WO 01/30995 | 5/2001 |
| WO | WO 03/035888 | 5/2003 |
| WO | WO 2005/014801 | 2/2005 |
| WO | WO 2005/066361 | 7/2005 |
| WO | WO 2007/023181 | 3/2007 |

OTHER PUBLICATIONS

Pompe et al., Maleic anhydride copolymers—a versatile platform for molecuar biosurface engineering, biomacromolecules 4(4);1072-79 (2003).*
Jeanpierre, M., "A Rapid Method for the Purification of DNA from Blood" vol. 15 No. 22 (1987) Nucleic Acids Research: 9611.
Johns, Jr., et al. "Purification of Human Genomic DNA from Whole Blood Using Sodium Perchlorate in Place of Phenol" (1989) Analytical Biochemistry: 276-278.
Blin, et al., "A General Method for Isolation of High Molecular Weight DNA from Eukaryotes" vol. 3 No. 9 (1976) Nucleic Acids Research: 2303-2308.
Maniatis, T., "Molecular Cloning" (A Laboratory Manual) (1982) Cold Spring Harbor Laboratory: 280-281.

* cited by examiner

*Primary Examiner* — Prabha Chunduru
*Assistant Examiner* — Suryaprabha Chunduru
(74) *Attorney, Agent, or Firm* — McBee Moore Woodward and Vanik IP LLC

(57) ABSTRACT

The present invention relates to an improved method for isolating nucleic acids, particularly genomic desoxyribonucleic acid (DNA) from blood.

17 Claims, 4 Drawing Sheets

Coating with various polymers (I)

METHOD FOR EXTRACTING NUCLEIC ACID FROM BLOOD

CROSS REFERECE TO RELATED APPLICATIONS

This is a §371 National Stage Application of International Application No. PCT/EP2006/064652 filed Jul. 25, 2006, which claims priority from German Application No. 10 2005 040259.3 filed Aug. 24, 2005.

BACKGROUND OF THE INVENTION

Field of the Invention

The present invention relates to an improved method for isolating nucleic acids, particularly genomic desoxyribonucleic acid (DNA) from blood.

Description of Related Art

Methods for the purification and isolation of nucleic acids, particularly genomic DNA, from whole blood are known from the prior art. Their method of application, however, has proved to be very complex and moreover very laborious and time consuming. Aside from this, the majority of methods, in addition to an isolation of the cell material or the cell nuclei, require a relatively long incubation time in the presence of proteinases, followed by—optionally several—phenol extractions (Molecular Cloning, A Laboratory Manual, Maniatis et al., pg. 9.17-9.18 as well as Nucl. Acid Res. 3, 2303-2306).

In view of these disadvantages, alternative methods have since been developed, which were intended not only to minimise the costs but also to increase the yield of nucleic acid or genomic DNA as well as their purity. Such methods are based on the use of chaotropic salts (Nucl. Acid Res. 15, 9611, 1987 as well as Anal. Biochem. 180, 276-278, 1989).

Thus, a method is disclosed, inter alia, in the European Patent Application EP 0 389 063, in which the blood sample under investigation is treated with a chaotropic substance in the presence of a matrix material—present in the form of particles—such as, for example silica. This was based on the knowledge that under these reaction conditions, the nucleic acids are liberated from the cells and then bind to suitable silica-based matrix materials. The matrix material possessing the nucleic acids can subsequently be separated from the reaction solution, e.g. by means of centrifugation. After separation of the supernatant liquid, the matrix material is subjected to one, or when necessary, a plurality of washing steps.

However, the above-described methods each have the disadvantages that they are very time consuming and include undesirable centrifugation steps that are inevitably linked to a material transfer that once again is laborious for each individual sample, and in addition is associated with a risk of contamination. In addition, these processes suffer the serious disadvantage that they cannot be automated.

Accordingly, the object of the present invention consists in avoiding the disadvantages of the methods from the prior art and provides a method for isolating nucleic acids, preferably genomic DNA, from blood, which in particular avoids time consuming and above all laborious centrifugation steps and which in particular can be automated. Moreover, the risk of contamination and the resulting biologically contaminated waste materials should be reduced to a minimum. In addition, the nucleic acids or the genomic DNA obtained in this way should be available in a form that makes them available for subsequent reactions—such as, for example, amplification reactions, particularly PCR—without additional process steps. This requirement stems from the need for genomic DNA for numerous different investigative methods such as e.g. genotyping, etc.

SUMMARY OF THE INVENTION

The requirement that is posed for the preliminary isolation of the genomic DNA is particularly that the genomic DNA, which inter alia represents the essential starting material for genotyping, has to be purified as quickly as possible and without delays and without being contaminated with foreign nucleic acids, can be employed in the desired subsequent reactions—in particular:

PCR based genotyping;
SNP analyses in the human genome;
Construction of a genetic fingerprint (forensics, criminology);
Diagnostic genotyping (e.g. cystic fibrosis; factor V Leiden);
Carrying out multiple or multiplex PCR from a sample for the identification of markers;
Restriction fragment length polymorphism based on primary PCR amplification;
Carrying out quantitative PCRs.

The above-described objects are achieved by means of the method proposed in the present invention, whereby the blood sample under analysis is firstly brought into contact with an erythrocyte lysis buffer in a reaction vessel that is provided with a coating that can adsorb the cell nuclei and mitochondria liberated by the lysis.

In addition, the adsorbing material can also be in the form of a matrix material that is not fixed to the boundary walls of the reaction vessel. Advantageously, the internally coated reaction vessel is designed in such a way that it allows an amplification reaction or PCR to be carried out, and—in a particular embodiment—allows an automated execution of the desired reaction of a plurality or a great number of samples.

DETAILED DESCRIPTION OF A PREFERRED EMBODIMENT

It has been surprisingly found that white blood cells as well as cell constituents, such as cell nuclei and mitochondria, liberated by means of the erythrocyte lysing, bind, in the presence of erythrocyte lysing buffers, to polymers possessing a polyanionic structure, in particular anionic polymers that exhibit functional groups of carboxylic acids or other acids—such as sulfonic or phosphonic acids or phenol as acid in the broadest sense. In this regard, the inventively added erythrocyte lysing buffers preferably lyse erythrocytes, the white blood corpuscles remaining intact, or are only lysed in so far as they remain as cell organella (cell nuclei and mitochondria). The cell organella do not have to remain completely intact, but at least in as far that an adsorption of the cell organella's surface onto the polymers possessing a polyanionic structure can occur. The destruction of the cell organella here is also not intended to be so advanced that the nucleic acid from the cell organella would be liberated, as it has been shown that the nucleic acid per se binds poorly to the cited polymers. Cell debris having DNA imbedded inside can be bound to the polymer matrix as well. All other interfering blood constituents—such as e.g. haemoglobin—can be separated as far as possible after the lysis by removing the reaction solution or by washing the polyanionic polymer matrix with suitable washing buffers.

The adsorption of the cell organella described above onto the matrix instead of directly binding the nucleic acids as is occasionally described in the prior art, as well as the use of polymers having polyanionic structures for this purpose have the advantage that the pH value in the lysis step does not have to be changed compared to the pH value in a PCR reaction optionally carried out subsequently, but may remain unchanged. Thereby it can be avoided to introduce further procedural steps serving neutralisation or adjustment of a different pH value.

In order to stabilise the blood sample and to prevent or to retard possible decomposition reactions, it can be advantageous to freeze the blood sample as soon as possible after collection and subject the frozen sample or the thawed sample to the method according to the invention.

The lysis buffers required for the lysis are known from the prior art and are also commercially available—e.g. "QIAGEN Buffer FG1", "QIAGEN Buffer C1" or Gentra RBC lysis solution. Indeed, in principle it is possible to use any buffer, whose constituents are capable of lysing erythrocytes. As an example, a buffer solution comprising 155 mM ammonium chloride and 10 mM potassium hydrogen carbonate may be cited. Further suitable buffers are known to the person skilled in the art and can comprise salts of inorganic or organic acids. They are preferably based on aqueous solutions of alkali or earth alkali metal halides—such as e.g. potassium chloride and magnesium chloride, supplemented by a pH-buffer, such as e.g. Tris, a detergent and optionally a sequestrant. Particularly preferred salts of inorganic or organic acids are ammonium salts such as e.g. ammonium chloride, ammonium sulfate or organic ammonium salts such as ammonium tartrate in concentrations between 100 and 500 mM, as well as anionic, neutral or cationic detergents in concentrations of 0.01 wt. % to 5 wt. %. Exemplary preferred detergents are SDS, Chaps, Tween 20, Triton or Catrimox.

In principle, all anionic structures formed from polymers are suitable as the coating materials, carboxylated polymers, copolymers, terpolymers or mixtures of these polymers being preferred. For example, copolymers based on styrene, vinyl methyl ether, linear or branched alkenes—such as e.g. 1-octadecene or isoprepene and maleic acid or acrylic acid, wherein the carboxyl functionalities can be optionally esterified to different degrees, can be employed. Preferred exemplary acrylic acid alkyl esters include the following: methyl acrylate, ethyl acrylate, vinyl acrylate, propyl acrylate, butyl acrylate, hexyl acrylate, octyl acrylate, decyl acrylate, dodecyl acrylate, myristyl acrylate, lauryl acrylate, cetyl acrylate, stearyl acrylate, methyl methacrylate, ethyl methacrylate, propyl methacrylate, butyl methacrylate, isobutyl methacrylate, hexyl methacrylate, 2-ethylhexyl acrylate, 2-ethylhexyl methacrylate, phenyl methacrylate, octyl methacrylate, decyl methacrylate, dodecyl methacrylate, myristyl methacrylate, lauryl methacrylate, cetyl methacrylate, where the acrylic acid methyl ester is particularly preferred.

The branched or linear $C_1$- to $C_{12}$ alkyl esters of acrylic or methacrylic acid are preferred, particularly methyl methacrylate, ethyl methacrylate, butyl methacrylate, 2-ethylhexyl methacrylate, methyl acrylate, ethyl acrylate, butyl acrylate and 2-ethylhexyl acrylate or maleic acid alkyl esters—such as e.g. maleic acid methyl ester.

It is also possible to employ other polymers that possess for example sulfonic acid or phosphonic acid groups or phenol groups or mixtures thereof, and which form polyanionic structures; polystyrene sulfonic acid in the form of the homopolymer or as a constituent of a copolymer may be cited as a representative example.

Although the phenolic compounds can also be constituents of the main chain, it is preferred that they are situated on the side chains of the polymer backbone. In general, the phenolic group can also be introduced into the polymer after the polymerisation. However, a particularly homogeneous distribution is obtained if the phenolic groups are already constituents of the monomer. For example, they can be bonded through substituents such as amine groups to polymerisable monomers like acrylic acid, methacrylic acid or their derivatives. In order to obtain a greater spacing of the phenol in the side chain from the polymer backbone, additional compounds can act as a bridge between the polymerisable constituent and the phenolic group. A phenolic compound that is particularly preferably used is tyramine.

Polyesters that are capable of forming a polyanionic structure illustrate further suitable polymers. In general, the monomers themselves can possess groups that after polymerisation constitute or form anionic sites. Moreover, the polyesters can also be subsequently provided with groups forming anions, e.g. through unsaturated sites or other functional groups present in the polyester.

Dicarboxylic acids, such as succinic acid, adipic acid, phthalic acid or maleic acid, and as alcohols, tartaric acid or other dihydric or trihydric alcohols that comprise at least one additional anionic functionality, are preferably used as the monomers. When maleic acid is used as the monomer, dihydric or trihydric alcohols—without additional anionic functionalities—can be used for the polymerisation, when the residual double bond of the maleic acid in the polymer is utilised, for example, to subsequently introduce anion forming groups, such as for example acrylic acid or methacrylic acid.

The copolymer capable of forming a polyanionic structure is preferably embodied by a carboxylated polymer based on styrene and maleic anhydride. In this regard, the copolymer possesses 5 to 95 wt. %, preferably 25 to 95 wt. % and particularly preferably 50 to 95 wt. % maleic acid units.

The copolymer capable of forming a polyanionic structure is preferably also likewise embodied by a carboxylated polymer based on methyl vinyl ether and maleic acid. The copolymer, for example, can be present as poly(methyl vinyl ether-alt-maleic acid),

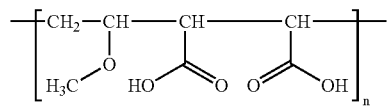

whose carboxylic groups can be partially esterified—e.g. with a methyl group.

Here, the poly(methyl vinyl ether-alt-maleic acid) copolymers can have a molecular weight in a range of $1.0 \cdot 10^3$ to $2.5 \cdot 10^6$, preferably $1.0 \cdot 10^4$ to $2.2 \cdot 10^6$ and particularly preferably in a range of $1.9 \cdot 10^6$ to $2.1 \cdot 10^6$.

The following are particularly preferred:
Poly(methyl vinyl ether-alt-maleic acid) MW: 1 980 000
Poly(isobutylene-alt-maleic acid) MW: 3 250 000
Polystyrene-co-maleic acid, 50 weight percent maleic acid
Polystyrene-co-maleic acid, 25 weight percent maleic acid
Polystyrene-co-maleic acid, 14 weight percent maleic acid
Polyisoprene-graft-maleic acid, 7 weight percent maleic acid
Poly(maleic acid-1-octadec-1-ene) in mole ratio 1:1
Poly(methyl vinyl ether-alt-maleic acid) MW: 1 250 000
Polystyrene-alt-maleic acid partially as the methyl ester
Poly(acrylic acid-co-acrylic acid methyl ester)

Polystyrenesulfonic acid

The manufacture of carboxylated polymers is well known from the prior art; as these polymers are employed in a great number of other technical applications, they are for the most part commercially available.

Further polymers can be manufactured by the radical polymerisation of monomers that possess carboxylic groups.

The polyanionic or carboxylated polymers can be deposited on the limiting wall/walls of the reaction vessel using many methods, be in the liquid state or in the form of a suspension in the mixture resulting from the lysis or be present in the form of a dipstick. The desired functionalised layer can be made by coating with a polymer melt. There is also the possibility—in so far as the reaction vessel is manufactured by injection moulding—to incorporate the polymer as an additive into the injection-moulding compound prior to injection moulding; likewise, it is possible to coat all or certain parts of the injection mould with the polymer prior to the injection moulding, the desired coating being obtained after formation of the reaction vessel. There is also the possibility to deposit a film of the polymer used to form the polyanionic structure onto the inner wall of the reaction vessel and e.g. manufacture the desired geometrical shape by means of the deep-drawing process. Preferably, the coating is carried out using the polyanionic polymer dissolved in a suitable solvent. In addition, there exists the possibility that the polymer is present in the solution firstly in the form of a precursor, from which the polymer with the desired structure is only formed in the course of the reaction.

There exists a further possibility—on choosing suitable polymers that are known to the person skilled in the art—to obtain the desired functionalisation of the surface of the initially manufactured unfunctionalised reaction vessel by using wet chemical processes (sulfuric acid/hydrogen peroxide) known from the prior art or by means of atmospheric pressure-plasma treatment.

In the subsequent step, for example, a typical amplification reaction—for example a PCR—can follow, which can be carried out under reaction conditions that are well known from the prior art. For this, no specific process adjustments are needed. On heating the reaction solution first to a temperature in a range from 45 to max. 100° C., preferably to a temperature in a range from 80 to 98° C. and particularly preferably to 94-96° C., the nucleic acids or the genomic DNA (thermal lysis) are liberated and thereby remain available in the subsequent PCR.

In a further embodiment, a coating or derivatisation of the vessel surface need not be effected if the polymer capable of forming polyanionic structures is incorporated as an additional component of the lysis buffer or the mixture being lysed. The binding of gDNA-containing cell constituents, like mitochondria and cell nuclei, then does not occur on the PCR vessel wall, but rather directly in the liquid phase. This leads to complexes consisting of the cited cell constituents and the carboxylated polymer, which can adhere to the vessel wall during the lysis and incubation in the PCR vessel. The coating therefore occurs simultaneously with the lysis i.e. cell constituents, already bound in the liquid phase, are precipitated out with the carboxylated polymer onto the vessel wall.

In all embodiments, the gDNA-containing cell constituents remain behind after the lysis and the optional washing of the polyanionic polymer, and can—as described—be further treated or detected and quantified.

In this way, in carrying out the analysis from the lysis of the blood sample to the start of the desired subsequent reaction in one vessel, the inventive method permits not only a significant reduction of the number of work steps and the risk of contamination of the sample, but also associated therewith is a significant reduction of biologically contaminated waste because the samples no longer need to be pipetted around.

A further material saving results from the fact that the present commercially available kit formats are dimensioned for the isolation of relatively large amounts of gDNA (typically 20 µg). For many application fields (e.g. the analysis of individual markers), this is over dimensioned. The inventive solution can be dimensioned for the preparation of 10 ng gDNA and therefore saves additional material. Both savings (less work steps, smaller kits) considerably reduce the total material usage of special plastic articles (e.g. punched silica membranes in composites with injection moulded polypropylene parts) and buffer solutions. Secondly, the reduced material usage also lowers the energy costs for the manufacture of the corresponding precursors.

Although it is preferred on grounds of work simplification and time saving or automation possibilities to leave out any centrifugation steps, there is still the possibility, even for the inventive method, to integrate an additional one or a plurality of centrifugation steps. Advantageously, these occur after contacting the blood sample with the erythrocyte lysis buffer and prior to removing the reaction mixture resulting from the lysis. It has been shown that the centrifugation causes the cell organella to bond significantly more strongly to the matrix than in the absence of a centrifugation step. This has the advantage that in the washing step, the loss of cell organella that detach themselves from the matrix and are removed together with the wash solution, and therefore the loss of isolated nucleic acid, is reduced.

When integrating a centrifugation step into the inventive method, it is not that the unwanted constituents of the lysis solution are sedimented and the desired constituents are transferred into another vessel, which can lead to contamination. But rather, the supernatant liquid which is supposed to be rejected, is separated, while the desired constituents are adsorbed and continue to remain in the vessel. Thereby, in the present method the risk of contamination is reduced.

Speeds of 100 to 500 000 rpm are advantageously employed for the centrifugation, further preferably 500 to 13 000 rpm and most preferably 1000 to 5000 rpm.

It has also been shown that with a reduced sample size, the washing step can be eliminated, without any loss in yield. For the typically used sample sizes of about 20 µl, such amounts of inhibitors are found in the sediment of the adsorbed or adhered cell organella, that subsequent applications such as PCR amplification can be compromised. Washing steps can reduce or totally prevent any interference from inhibitors and increase the yield. However, a reduction in the sample size also means that the quantity of inhibitors is reduced, even in the absence of a washing step. At the same time, the binding of the nucleic acid to the matrix, particularly in the additional use of one or a plurality of centrifugation steps, appears to be so strong that no reduction in yields occurs.

A further subject matter of the present invention is a kit for obtaining nucleic acid from samples comprising cell organella that comprise nucleic acids, including a) a matrix material, present in solid form on the inner wall of one or a plurality of empty reaction vessels or as a solid, in solution or in a dispersed state, and which is capable of adsorbing cell organella, b) one or a plurality of erythrocyte lysis buffers, c) optionally, one or a plurality of reaction vessels when the matrix material is not present on the inner wall of the one or plurality of empty reaction vessels, d) optionally, one or a plurality of wash solutions, e) optionally, reagents for carrying out PCR reactions and f) optionally an instruction manual.

The above-described polymer, copolymer or terpolymer, capable of forming a polyanionic structure, is preferably used as the matrix material.

Preferably, the reaction vessels concern sample vessels, as are used in the prior art for the purification of biological samples. In this regard, they can be individual vessels or conglomerates of a plurality of vessels, such as for example 48 or 96 well plates or other vessel conglomerates known from the prior art.

The matrix material is preferably situated on the inner wall of these vessels. It can be either fixed to or adsorbed on the wall in advance as described above, such that one or a plurality of already coated sample vessels are made available. There is also the possibility that the matrix material is made available as a solid, in solution or in the dispersed state and is added during the above-described method for obtaining the nucleic acid. It can be added both to the lysis solution and to the sample, added to the empty reaction vessel or added to the lysate.

The matrix material and the material of the reaction vessel should be selected in such a way that the matrix material after the lysis is fixed to or adsorbed on the inner walls of the reaction vessel. When using the above-described polymers, commercial sample vessels, in particular made of plastic, can be used. The use of PCR reaction vessels has the advantage that the prepared samples for carrying out the PCR reaction need not be transferred again.

Particularly when the matrix material is not yet present as the sample vessel coating, one or a plurality of sample vessels can also be included in the kit.

The following examples are intended to exemplify the present invention. The examples embody solely advantageous embodiments of the invention without limiting it in any way.

The following is to be learnt from FIG. 1:

8 samples were amplified in PCR vessels according to example 10, which were provided with a poly (vinyl methyl ether-maleic acid) coating according to example 9. The obtained results are presented as threshold values (Ct values) in FIG. 1.

The following is to be learnt from FIG. 2:

Blood from 5 donors was collected in each of 4 different blood extraction tubes. Four preparations were carried out in PCR vessels for each sample/blood extraction tubes—as described in example 10. A sequence fragment of the human β-Aktin gene was amplified in the qPCR using TaqMan probes. The bar chart of FIG. 2 illustrates the results of the quantitative PCR. Each bar represents the ct value averaged from four PCR vessels.

EXAMPLES

Figure 1:
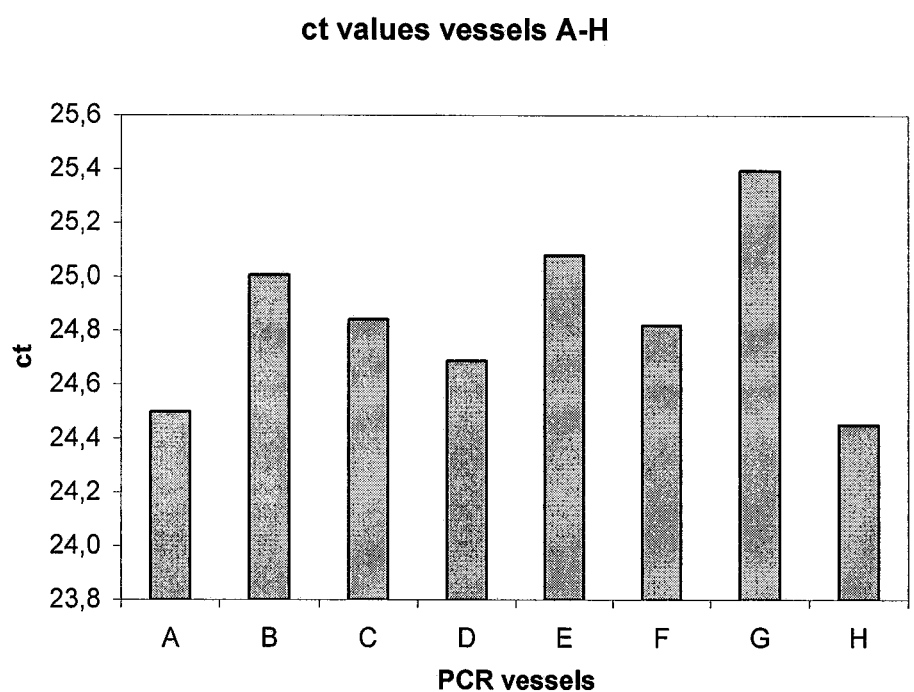

1) N-(2-Hydroxyethyliminodiacetic acid) (250 mg) was added to 50 ml of polystyrene-co-maleic acid with a 14% weight content of maleic anhydride dissolved in DMSO (20 mg/ml dimethyl sulfoxide) and heated to 60° C. for 45 minutes.

Subsequent dilution with ten times DMSO afforded a ready for use solution for coating reaction vessels for the amplification reactions or PCR.

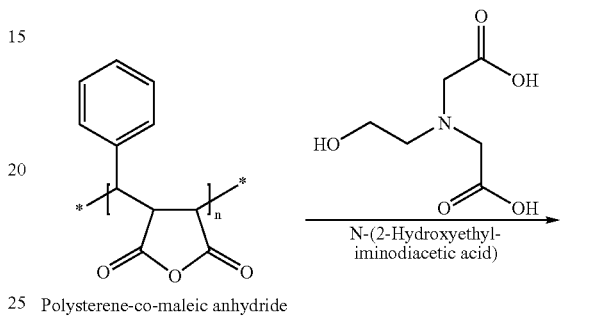

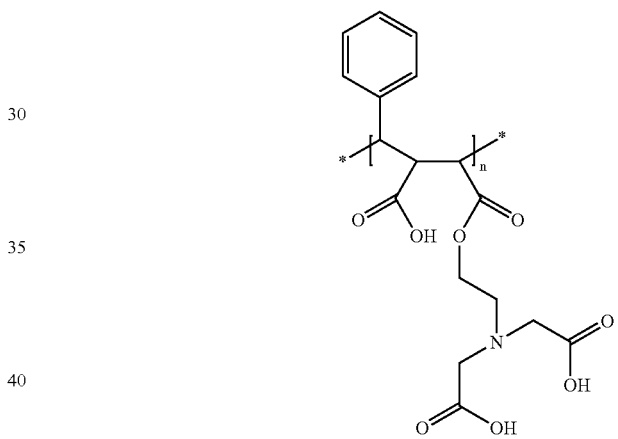

2) N-(2-Hydroxyethyl)imino bis(methylphosphonic acid), (1.3 g) was added to 50 ml of polystyrene-co-maleic acid with a 50% weight content of maleic anhydride dissolved in DMSO (20 mg/ml dimethyl sulfoxide), and heated to a temperature of 60° C. for 1 hour. Subsequent dilution with ten times DMSO afforded a ready for use solution for coating reaction vessels for amplification reactions or PCR.

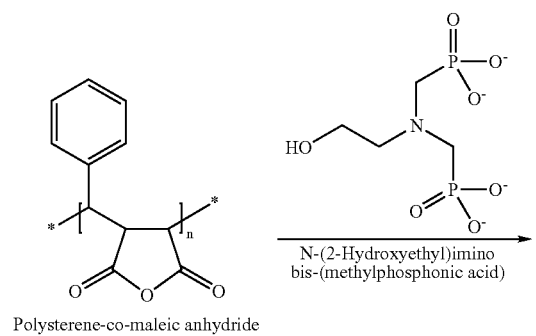

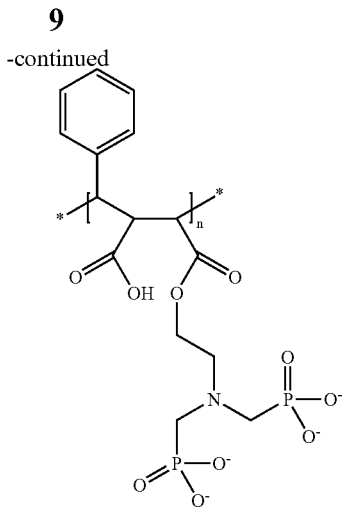

3) N-Me-PVA (N-methyl-polyvinylamine), (50 mg, 0.877 mmol), was dissolved in 2 ml water and after adding 1.31 mmol of bromoacetic acid (180 mg, 1.5 eq.) and 50 µl TEA (triethylamine), was shaken for 12 hours. This afforded a ready for use solution for coating reaction vessels for the amplification reactions or PCR.

4) Bromoacetic acid, 630 mg (0.454 mmol, 0.8 eq.) was added to polyvinyl alcohol, 0.2 g (MW 9000-10 000) and after the addition of $K_2CO_3$, 1.2 g (9.08 mmol, 1.5 eq.), was shaken for 12 hours. This afforded a ready for use solution for coating reaction vessels for amplification reactions or PCR.

5)
a) Synthesis of N-(4-methylphenol)amide of methacrylic acid

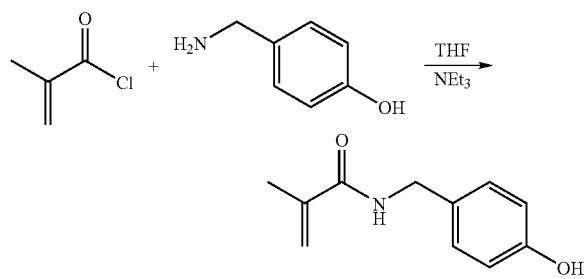

302 mg (2.2 mmol) Tyramine were dissolved in 5 mL THF, reacted with 570 µL triethylamine and cooled to 0° C. After a slow addition of 208 mg (2 mmol) methacroyl chloride, the mixture was stirred overnight. It was then hydrolysed with 1M hydrochloric acid and extracted three times with ethyl acetate. The collected organic phases were dried over sodium sulfate and the solvent was then removed under reduced pressure. (1.52 mmol, yield 76%)

a) Synthesis of N-(4-methylphenol)amide of polymethacrylic acid

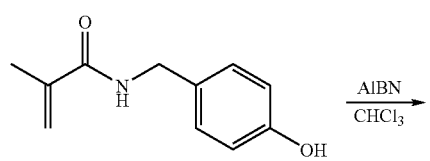

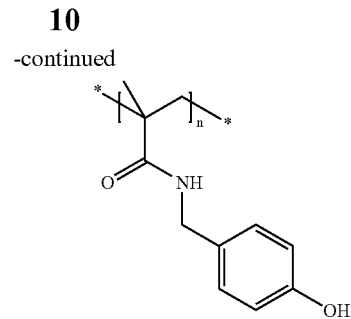

The monomer resulting from a) was dissolved in chloroform and after the addition of a spatula tip of AlBN was heated under reflux for 5 hours. Another spatula tip of AlBN was then added and the mixture was heated overnight. The mixture was then hydrolysed and twice extracted with dichloromethane. The collected organic phases were dried over sodium sulfate and the solvent was then removed under reduced pressure. A reddish resin was obtained that was not purified further. A coating solution at a concentration of 60 mg/ml in ethanol was prepared.

6)
a) Synthesis of 2-hydroxy-3-aminopropyl-N-(4-methylphenol) methacrylate

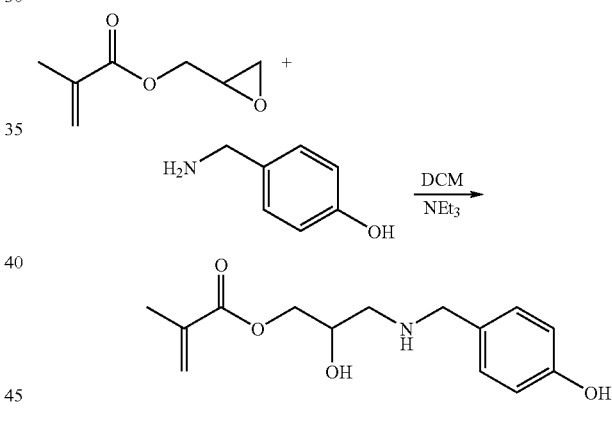

300 µL triethylamine were slowly added to 302 mg (2.2 mmol) tyramine and 284 mg (2 mmol) methacrylic acid glycidyl ester in 5 mL dichloromethane (DCM) and stirred at room temperature overnight. The mixture was then hydrolysed with 1M hydrochloric acid and extracted three times with ethyl acetate. The collected organic phases were dried over sodium sulfate and the solvent was then removed under reduced pressure. (1.36 mmol, yield 68%)

b) Synthesis of poly 2-hydroxy-3-aminopropyl-N-(4-methylphenol) methacrylate

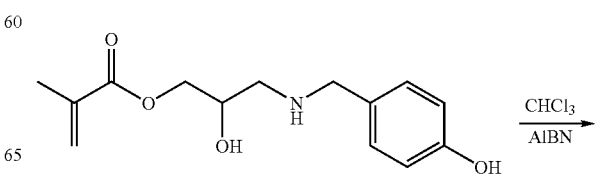

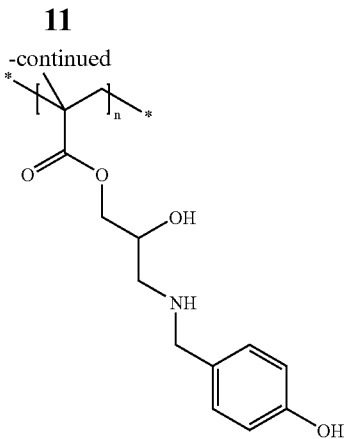

The monomer was dissolved in chloroform and after the addition of a spatula tip of AIBN was heated under reflux for 5 hours. Another spatula tip of AIBN was then added and the mixture was heated overnight. The mixture was then hydrolysed and twice extracted with dichloromethane. The collected organic phases were dried over sodium sulfate and the solvent was then removed under reduced pressure. A light yellow resin was obtained that was purified by means of dialysis.

A coating solution (analogous to example 9) was prepared using water as the solvent.

7)
Synthesis of polymaleic acid-N-(4-methylphenol)amide

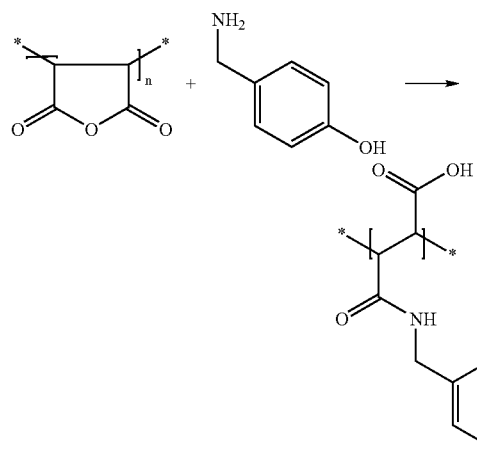

500 mg Poly(maleic anhydride) (~5.1 mmol maleic anhydride) were admixed with 680 mg (4.95 mmol) tyramine and stirred for 12 hours at 60° C. Purification was then carried out by dialysis.

A coating solution at a concentration of 60 mg/ml in demineralised water was prepared.

8) Polytartaric Acid Succinate

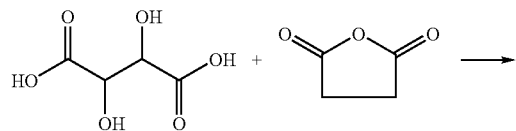

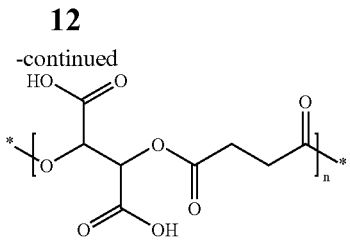

1.5 g (10 mmol) tartaric acid were mixed with 1 g (10 mmol) succinic anhydride and heated for 5 hours to 60° C. There resulted a pale yellow resin that was purified by dialysis.

A coating solution at a concentration of 60 mg/ml in demineralised water was prepared.

9) Coating Procedure 20 mg Poly(methyl vinyl ether-alt-maleic acid) were dissolved in 10 ml demineralised water.

After the polymer was completely dissolved, 50 μl of the aqueous polymer solution was pipetted into each commercially available PCR vessel (8 strips) made of polypropylene. After 20 minutes incubation time at room temperature, the aqueous polymer solution was pipetted out of the PCR vessels. The vessels were then rinsed once with 120 μl water and dried at 40° C.

10) Preparation of the Blood Sample in the PCR Vessel.

Figure 2:
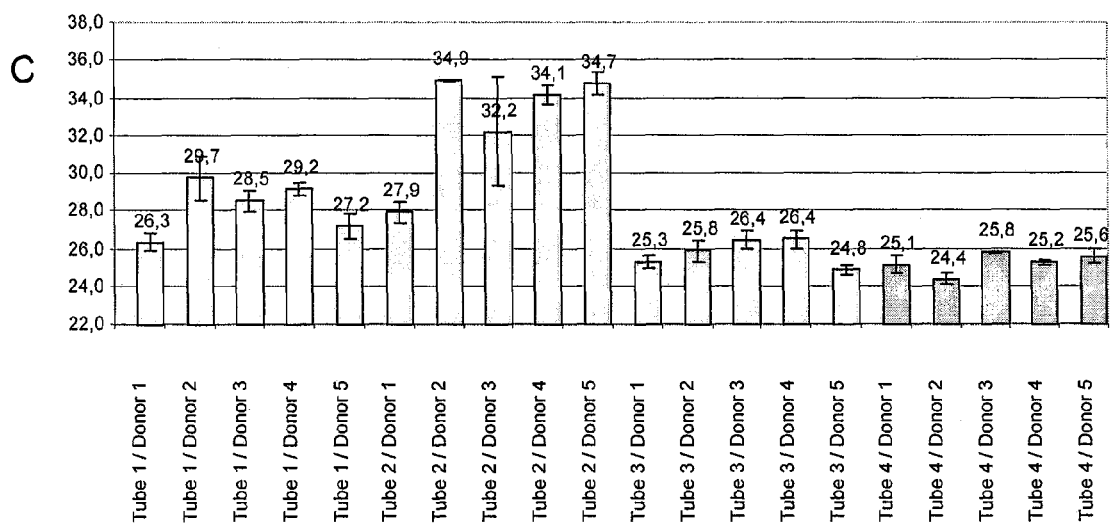

50 μl Lysis buffer (155 mM $NH_4Cl$, 10 mM $KHCO_3$ in water) was placed in the cavities of each PCR vessel and 10 μl blood was pipetted in. The blood sample was thoroughly mixed with the lysis buffer by pipetting in and out ten times. After an incubation time of 5 minutes, the solution was again mixed and after a further 15 minutes the liquid contents of the PCR vessel were rejected, then washed once with 120 μl wash buffer (1 mM Tris-HCl, 0.5 mM EDTA, pH 7.4+0.05% Nonidet P-40) and rejected residue-free. Finally, 25 μl of a PCR reaction mixture were added and a quantitative real time PCR (RT-PCR) was carried out. The corresponding results are presented in FIG. 2.

11)
In a further experiment in a 96 well plate, 2 rows of 8 wells were each coated with the following polymers:
1+2: Poly(methylacrylic acid-N-(4-methylphenol)amide) from example 5
3+4: Polymaleic acid-N-propylamide
5+6: Poly(maleic acid-N-(4-methylphenol)amide) from example 7
7+8: Polytartaric acid succinate from Example 8
9+10: Poly(isobutylene-alt-maleic acid)
11: Poly(methyl vinyl ether-alt-maleic acid) from Example 9

The coating solutions described in each of the examples were prepared for coating. The polymaleic acid-N-propylamide solution was prepared in a concentration of 40 mg/ml in demineralised water. The poly(isobutylene-alt-maleic acid) was prepared in a concentration of 5 μl/ml in 1N KOH.

After the polymer was completely dissolved, 50 μl of each polymer solution was pipetted into the commercially available PCR vessels (8 strips) made of polypropylene. After 5 minutes incubation time at room temperature, the liquid contents of the PCR vessels were pipetted off. The vessels were then dried at 50° C. for one hour.

Figure 3:
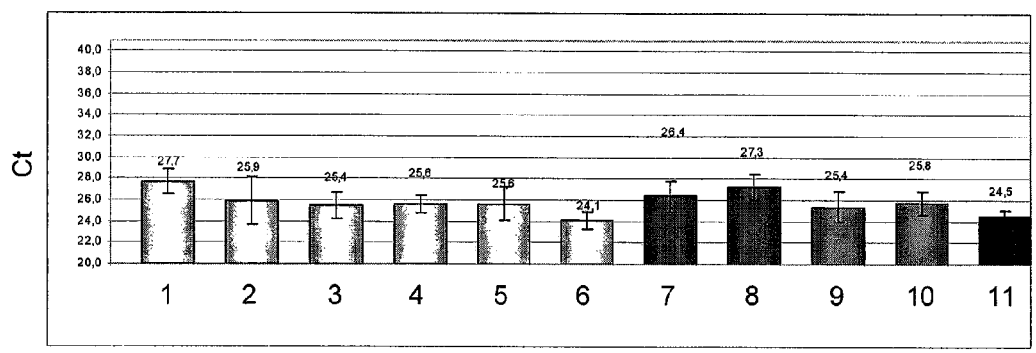
FIG. 3 shows the Ct values of the PCR reactions of samples prepared according to example 11 in sample vessels that were coated with various polymers.
Figure 4:
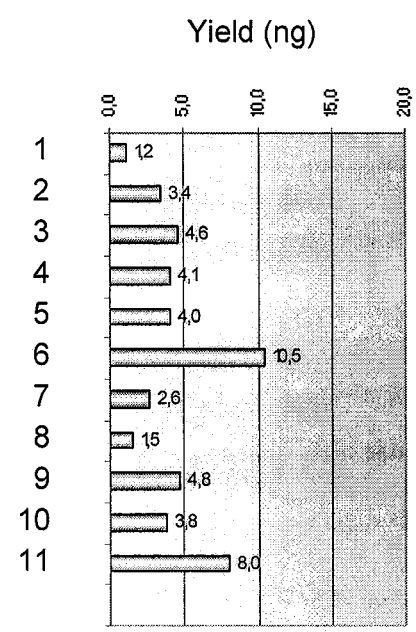
FIG. 4 shows the absolute quantities of nucleic acid resulting from the amplification according to example 11, calculated from a calibration curve.

Then, a preparation of one blood sample was carried out, together with a subsequent PCR reaction according to the description of example 10. The Ct values obtained for the polymers used are shown in FIG. 3; the calculated absolute yields obtained using a calibration curve, are shown in FIG. 4.

The results illustrated in both Figures show that polyphenols and polyesters are suitable coating materials according to the present invention.

The invention claimed is:

1. A method for obtaining nucleic acid from blood, comprising bringing a blood sample in a reaction vessel into contact with an erythrocyte lysis buffer in the presence of a matrix that can adsorb cell organella, wherein the matrix is adsorbed on a wall of the reaction vessel, and wherein the matrix comprises a polymer, copolymer or terpolymer or a mixture thereof capable of forming a polyanionic structure,
removing a reaction mixture resulting from contact with the lysis buffer,
optionally washing and/or heating the matrix to a temperature at which nucleic acids from the adsorbed blood constituents are released and
optionally subjecting the nucleic acid to a subsequent reaction.

2. A method according to claim 1, wherein the nucleic acid embodies genomic DNA.

3. A method according to claim 1, wherein (i) the matrix is present in solid form on a wall of the reaction vessel or as a dipstick, and/or (ii) the matrix before contact with the lysis buffer is present in a liquid or dispersed form and after contact with the lysis buffer is adsorbed on the walls of the reaction vessel.

4. A method according to claim 1, wherein the polymer, copolymer or terpolymer capable of forming a polyanionic structure is a polycarboxylate or a carboxylated polymer or a polyester capable of forming a polyanionic structure.

5. A method according to claim 4, wherein the polymer, copolymer or terpolymer capable of forming a polyanionic structure is a carboxylated polymer based on vinyl methyl ether, maleic anhydride, styrene, linear or branched alkenes or acrylic acid and its derivatives.

6. A method according to claim 5, wherein the acrylic acid derivative is a linear or branched $C_1$-$C_{12}$ alkyl ester of acrylic or methacrylic acid with one to twelve carbon atoms.

7. A method according to claim 4, wherein the polymer, copolymer or terpolymer capable of forming a polyanionic structure comprises a phosphonic acid group or sulfonic acid group or phenol group and/or a mixture thereof.

8. A method according to claim 7, wherein the polymer comprising sulfonic acid group is polystyrenesulfonic acid or a copolymer/terpolymer with polystyrenesulfonic acid.

9. A method according to claim 4, wherein the polymer, copolymer or terpolymer capable of forming a polyanionic structure is a carboxylated polymer based on styrene and maleic anhydride.

10. A method according to claim 9, wherein the copolymer comprises 5 to 95 weight percent maleic acid units.

11. A method according to claim 4, wherein the copolymer or terpolymer capable of forming a polyanionic structure is a carboxylated polymer based on methyl vinyl ether and maleic acid.

12. A method according to claim 11, characterised in that the copolymer poly(methyl vinyl ether-alt-maleic acid) is present as the partial methyl ester.

13. A method according to claim 1, wherein the erythrocyte lysis a buffer comprises at least one salt of an alkaline, pseudoalkaline or earth alkaline metal salt with an inorganic or organic acid, at least one cationic detergent and optionally a substance for buffering pH.

14. A method according to claim 1, wherein water and/or a buffer comprising TRIS, chelating agents and optionally a detergent are employed as a wash buffer.

15. A method according to claim 1, wherein blood constituents in said blood sample adsorbed on the matrix after washing are heated, optionally in aqueous solution to a temperature in an interval of 45 to 100° C., and optionally subjected to an amplification reaction and/or PCR.

16. A method according to claim 1, wherein after contacting the blood sample with the erythrocyte lysis buffer and the matrix, and prior to removing the reaction mixture resulting from the lysis, a centrifugation step is conducted.

17. A method of claim 11, wherein the carboxylated polymer based on methyl vinyl ether and maleic acid comprises a copolymer poly(methyl vinyl ether-alt-maleic acid),

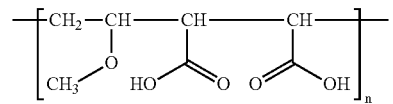

wherein the poly(methyl vinyl ether-alt-maleic acid) copolymer has a molecular weight in the range from $1.010^3$ to $2.510^6$.

* * * * *